US010093988B2

(12) United States Patent
Taberlet et al.

(10) Patent No.: US 10,093,988 B2
(45) Date of Patent: Oct. 9, 2018

(54) UNIVERSAL PRIMERS AND THE USE THEREOF FOR THE DETECTION AND IDENTIFICATION OF AMPHIBIA/FISH SPECIES

(75) Inventors: Pierre Taberlet, La Terrasse (FR); Eric Coissac, Arvillard (FR); Tiayyba Riaz, Grenoble (FR)

(73) Assignees: UNIVERSITE GRENOBLE ALPES, Saint Martin d'Heres (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 780 days.

(21) Appl. No.: 14/122,459

(22) PCT Filed: May 25, 2012

(86) PCT No.: PCT/FR2012/000213
§ 371 (c)(1),
(2), (4) Date: Feb. 13, 2015

(87) PCT Pub. No.: WO2012/160278
PCT Pub. Date: Nov. 29, 2012

(65) Prior Publication Data
US 2015/0159226 A1 Jun. 11, 2015

(30) Foreign Application Priority Data

May 26, 2011 (FR) .................................... 11 54608

(51) Int. Cl.
*C12Q 1/68* (2018.01)
*C12Q 1/6888* (2018.01)

(52) U.S. Cl.
CPC ..... *C12Q 1/6888* (2013.01); *C12Q 2600/158* (2013.01)

(58) Field of Classification Search
None
See application file for complete search history.

(56) References Cited

FOREIGN PATENT DOCUMENTS

GB 2374597 10/2002
WO 2008056325 5/2008

OTHER PUBLICATIONS

Infante et al. (Novel method for the authentication of frigate tunas (*Auxis thazard* and *Auxis rochei*) in commercial canned products, J Agric Food Chem. Dec. 15, 2004;52(25):7435-43).*

Rasmussen et al. (DNA-Based Methods for the Identification of Commercial Fish and Seafood Species, Comprehensive Reviews in Food Science and Food Safety, vol. 7, Issue 3, Jun. 2008, pp. 280-295).*
Dimmick et al. (A Molecular and Morphological Perspective on the Phylogenetic Relationships of the Otophysan Fishes, Mol Phylogenet Evol. Aug. 1996;6(1):120-33).*
Kitano et al. (Two universal primer sets for species identification among vertebrates, Int J Legal Med. Sep. 2007;121(5):423-7. Epub Jul. 15, 2006).*
Merriam-Webster, definition of batrachian, available at http://www.merriamwebster.com/dictionary/batrachian, accessed Sep. 8, 2016.*
Taberlet P, Coissac E, Hajibabaei M, Rieseberg LH (2012) Environmental DNA. Molecular Ecology, 21, 1789-1793.
Riaz T, Shehzad W, Viari A, Pompanon F, Taberlet P, Coissac E (2011) ecoPrimers: inference of new DNA barcode markers from whole genome sequence analysis. Nucleic Acids Research, 39, e145.
Clarke LJ, Soubrier J, Weyrich LS, Cooper a (2014) Environmental metabarcodes for insects: in silico PCR reveals potential for taxonomic bias. Molecular Ecology Resources, 14, 1160-1170.
Martin et al; Real time polymerase chain reaction detection of fishmeal in feedstuffs, Journal of AOAC International, AOAC International, Arlington, VA, vol. 93; No. 6; Nov. 1, 2010; pp. 1768-1777.
Pereira et al.; Analysis of inter-specific mitochondrial DNA diversity for accurate species identification; International Congress Series, Excerpta Medica, Amsterdam, NL vol. 1288; Apr. 1, 2006 p. 105.
International Search Report, PCT/FR2012/000213, dated Sep. 19, 2012.
"Molecular cloning: a laboratory manual", published by: Cold Spring Harbor Laboratory Press, Cold Spring Harbor, NY, 1989 (Book not included).
Kitano et al., Two universal primer sets for species identification among vertebrates, International Journal of Legal Medicine, Springer, Berlin, DE, vol. 121, No. 5, Jul. 15, 2006 (Jul. 15, 2006) pp. 423-427.

* cited by examiner

Primary Examiner — Aaron A Priest
(74) Attorney, Agent, or Firm — Porzio Bromberg & Newman P.C.

(57) ABSTRACT

The invention relates to oligonucleotides and to the use thereof as universal primers for the detection and identification of *amphibia*/fish species, especially in complex and deteriorated substrates. The invention also relates to a method for detecting and identifying *amphibia*/fish species in samples collected from the environment (ground, water, faeces) or from industry (especially transformed products). The invention further relates to a kit for said detection.

9 Claims, No Drawings
Specification includes a Sequence Listing.

UNIVERSAL PRIMERS AND THE USE THEREOF FOR THE DETECTION AND IDENTIFICATION OF AMPHIBIA/FISH SPECIES

The present invention relates to oligonucleotides and to the use thereof as universal primers for the detection and identification of *batrachian* and/or fish species, in particular in complex and degraded substrates.

Taxonomic identification based on DNA analysis is an approach commonly used today to identify species within a mixture. An international consortium called Barcode for Life has been created, with the objective of enabling the detection of animal or plant species from a DNA sequence. For identifying animals, the approach consists in amplifying and then sequencing a sequence of 648 base pairs of the mitochondrial cytochrome c oxidase 1 ("CO1") gene. CO1 has been found to be effective for identifying birds, butterflies, fish, flies and other animal groups (Hebert et al., 2003). For plants, the situation is more complex and two other chloroplast DNA sequences, matK and rbcL, have been proposed (Hollingsworth et al., 2009). However, it turns out that the fragments chosen according to this method are too long (greater than 500 nucleotides) to be used in degraded substrates. As it happens, in a very large number of situations, the substrates to be analyzed contain degraded DNA, often with fragments of less than 100 nucleotides. It is in particular the case with samples collected from the environment (soil, water, feces) or templates used in industry, for example animal meals or mass-produced ready meals from the food industry.

One solution for detection and specific identification consists in analyzing informative DNA fragments of small size (Poinar et al., 1998; Willersley et al., 2003; Willersley et al., 2007). Primers have thus been defined in order to amplify shorter plant DNA fragments in frozen soil samples. Nevertheless, the primers make it is possible to identify plant families but not plant species. In addition, the primers were not chosen so as to amplify sequences sufficiently conserved in the plant kingdom to enable the amplification of any plant species. In other words, these primers are not truly universal.

WO 2006/024751 describes a method for simultaneously detecting, in a sample of biological material, the possible presence of biological matter by polymerase chain reaction (PCR) and then hybridization with probes. The primers described are highly degenerate (practically each codon comprises a degenerate nucleotide) and consequently lack specificity for the amplification of vertebrate DNA.

Patent EP1797201 provides oligonucleotides which allow the detection and identification of plants in complex or degraded substrates because the region amplified is both short and very variable. More specifically, the region amplified corresponds to a variable region of the intron of the tobacco chloroplastic trnL gene. In this regard, reference is also made to the article by Taberlet et al., 2007.

The primers described in said patent are specific for plant species and they do not allow the identification and detection of *batrachian* and/or fish species in complex or degraded substrates.

The present invention proposes novel oligonucleotides and the uses thereof as universal primers for the identification and detection of *batrachian* and/or fish species. These primers make it possible at the same time to amplify a short region (less than 95 base pairs), a region which is very variable between *batrachian* and/or fish species and a region which at the same time has very conserved flanking regions allowing amplification using a one and only pair of primers. Thus, these primers can be used in complex and degraded mixtures, for example soil, feces and water samples. Such primers in particular have applications in the analysis of mass-produced ready meals which may contain *batrachian* and/or fish mixtures, but also for the analysis of the diets of carnivores using feces.

More specifically, these primers make it possible to amplify a 12S region of mitochondrial DNA. It is particularly advantageous to have primers which allow the amplification of mitochondrial DNA since said DNA represents a very accessible target in the case of degraded substrates. Furthermore, mitochondrial DNA is repeatedly present in each cell.

The universal primers which are the subject of the present invention are particularly advantageous since they are extremely specific for batrachians and/or fish and do not amplify any other taxonomic group.

DESCRIPTION OF THE INVENTION

The invention relates to a pair of oligonucleotides, according to which the first oligonucleotide selectively hybridizes to the sequence SEQ ID NO. 4 and the second nucleotide selectively hybridizes to the sequence SEQ ID NO. 5 or to the sequence SEQ ID NO. 6 under sufficient stringency conditions for the amplification of a variable region of the mitochondrial 12S gene of batrachians and fish by polymerase chain reaction (PCR).

According to one aspect of the invention, the amplified region of the mitochondrial 12S gene comprises less than 95 nucleotides.

According to another aspect of the invention, the first oligonucleotide has a nucleotide sequence SEQ ID NO. 1 and the second oligonucleotide has a nucleotide sequence SEQ ID NO. 2 or SEQ ID NO. 3.

According to yet another aspect of the invention, the region amplified by polymerase chain reaction has a nucleotide sequence selected from the group consisting of SEQ ID NOS. 14-48.

The present invention also provides a mixture of primers for the amplification of a variable region of the mitochondrial 12S gene of batrachians and fish by polymerase chain reaction (PCR), comprising the amplification primers according to SEQ ID NO. 1, SEQ ID NO. 2 and SEQ ID NO. 3.

According to one aspect of the invention, the mixture of primers also comprises a blocking primer according to SEQ ID NO. 7.

The present invention also relates to a method for amplifying a region of the mitochondrial 12S gene of *batrachian* and fish species, comprising the following steps:

a) a sample which may contain DNA of a *batrachian* and/or fish species is provided;

b) an amplification chain reaction is carried out using a pair of oligonucleotides as claimed in the invention or a mixture of primers as claimed in the invention.

The present invention also relates to a method for detecting a *batrachian* and/or fish species in a sample, comprising the following steps:

a) a sample which may contain DNA of a *batrachian* and/or fish species is provided;

b) the total DNA contained in the sample is isolated;

c) an amplification chain reaction is carried out using a pair of oligonucleotides as claimed in the invention or a mixture of primers as claimed in the invention; and d) the possible presence of an amplification product is detected.

The present invention also relates to a method for detecting and identifying a *batrachian* and/or fish species in a sample, comprising the following steps:

a) a sample which may contain DNA of a *batrachian* and/or fish species is provided;

b) the total DNA contained in the sample is isolated;

c) an amplification chain reaction is carried out using a pair of oligonucleotides as claimed in the invention or a mixture of primers as claimed in the invention;

d) the presence of an amplification product is detected; and e) the sequence of the amplification product is determined in order to identify the *batrachian* and/or fish species contained in the sample.

The present invention also provides a kit for the detection of a *batrachian* and/or fish species in a sample, comprising a pair of oligonucleotides as claimed in the invention or a mixture of primers as claimed in the invention, and at least one additional reagent.

According to one aspect of the invention, the kit comprises another pair of oligonucleotides chosen from the following pairs of primers:

amplification primers according to SEQ ID NO. 8 and SEQ ID NO. 9, optionally with a blocking primer according to SEQ ID NO. 10; and amplification primers according to SEQ ID NO. 11 and SEQ ID NO. 12, optionally with a blocking primer according to SEQ ID NO. 13.

The present invention also relates to the use of at least one part of the region of the mitochondrial 12S gene of batrachians and/or fish corresponding to positions 3525 to 3618 of the mitochondrial 12S gene of *Rana nigromaculata* (NC_002805), for detecting *batrachian* species and/or fish species.

According to one aspect of the invention, the part of said region corresponds to positions 3542 to 3595 of the mitochondrial 12S gene of *Rana nigromaculata* (NC_002805) and is selected from the group consisting of SEQ ID NOS. 14-48.

DESCRIPTION OF THE SEQUENCE LISTING

SEQ ID NO. 1: BT_F primer
SEQ ID NO. 2: B_R primer
SEQ ID NO. 3: T_R primer
SEQ ID NO. 4: sequence of the region complementary to the BT_F primer
SEQ ID NO. 5: sequence of the region complementary to the B_R primer
SEQ ID NO. 6: sequence of the region complementary to the T_R primer
SEQ ID NOS. 8-9 and 11-12: pair of additional amplification primers which can be added to the detection kit as claimed in the invention SEQ ID NOS. 7, 10 and 13: blocking primers
SEQ ID NOS. 14-48: examples of amplified variable sequences of various *batrachian* and fish species
SEQ ID NOS. 49-50: variants of the BT_F primer
SEQ ID NOS. 51-52: variants of the B_R primer Pair of Oligonucleotides The present invention thus relates to oligonucleotides derived from two conserved regions of a mitochondrial 12S gene present in batrachians and fish. These oligonucleotides can be used as primers for the amplification and thus the detection of *batrachian* and fish DNA in a sample which may contain such a DNA. Indeed, the conserved regions from which the polynucleotides of the present invention are derived flank a region which is both short and very variable of *batrachian* and fish DNA, more specifically a short and variable region in the mitochondrial 12S gene of batrachians and fish. The variability of this region between *batrachian* and fish species can thus be used for detecting and identifying *batrachian* and fish species.

According to the present invention, the term "oligonucleotide" is intended to mean a single-stranded nucleotide chain, or the chain complementary thereto, which may be of DNA or RNA type, or a double-stranded nucleotide chain which may be of complementary or genomic DNA type. According to one embodiment, the oligonucleotides of the invention are of DNA type, in particular double-stranded DNA type. The term "oligonucleotide" also denotes modified polynucleotides. Modified oligonucleotides are, for example, oligonucleotides conjugated to binding reagents (biotin, for example) or to labeled reagents (fluorescent labels, for example). Conventionally, the binding reagents or the labeled reagents conjugated to the oligonucleotides facilitate the purification or detection of these oligonucleotides.

The oligonucleotides of the present invention can be prepared by chemical synthesis or by conventional molecular biology techniques as described by Sambrook, Fristsch and Maniatis, in their manual entitled "Molecular cloning: a laboratory manual", published by: Cold Spring Harbor Laboratory Press, Cold Spring Harbor, N.Y., 1989. The oligonucleotides of the present invention can also be isolated or purified from their natural environment.

The term "polynucleotide" can here be used as a replacement for the term "oligonucleotide" with equivalent meaning.

The term "primer" is intended to mean a short oligonucleotide sequence which, when hybridized with a nucleic acid template, allows a polymerase to start the synthesis of a new strand of DNA. The strand produced from the primer is complementary to the strand used as template. Primers are in particular used in polymerase chain reaction (PCRs).

The term "*batrachian* species" or "fish species" is intended to mean any organism which is respectively part of the *batrachian* kingdom or of the fish kingdom.

The present invention thus relates to a pair of oligonucleotides according to which the first oligonucleotide selectively hybridizes to a very conserved region of the mitochondrial 12S gene of batrachians and fish and the second nucleotide selectively hybridizes to another very conserved region of the mitochondrial 12S gene of batrachians or to another very conserved region of the mitochondrial 12S gene of fish under sufficient stringency conditions for the amplification of the variable region of the mitochondrial 12S gene of batrachians and fish by polymerase chain reaction (PCR), for example under high stringency conditions. The sequence of the first conserved region corresponds to the sequence of the BT_F primer (SEQ ID NO. 1) and of the sequence complementary thereto (SEQ ID NO. 4). The sequence of the second conserved region corresponds to the sequence of the B_R primer (SEQ ID NO. 2) and of the sequence complementary thereto (SEQ ID NO. 5). Alternatively, the sequence of the second conserved region corresponds to the sequence of the T_R primer (SEQ ID NO. 3) and of the sequence complementary thereto (SEQ ID NO. 6).

By way of example, in *Rana nigromaculata*, the first oligonucleotide of the present invention is at position 3525 to 3541 of the sequence NC_002805, and the second oligonucleotide of the invention is at position 3596 to 3618 of this same sequence. In *Gadus morhua*, the first oligonucleotide of the present invention is at position 904 to 920 of the sequence NC_002081, and the second oligonucleotide of the invention is at position 983 to 1002 of this same sequence.

Those skilled in the art know the DNA amplification reactions and the stringency conditions which allow selective amplification of a sequence. Those skilled in the art know in particular the hybridization temperature conditions and the hybridization buffer composition conditions.

Those skilled in the art will thus be able to easily define different variants of the BT_F (SEQ ID NO. 1) and B_R (SEQ ID NO. 2) or T_R (SEQ ID NO. 3) primers using routine techniques. These variants hybridize to the reference sequences and allow the selective amplification of the variable region of interest of the mitochondrial 12S DNA.

Two possible variants of the BT_F primer (SEQ ID NO. 1) are represented in sequences SEQ ID NOS. 49-50. Two possible variants of the B_R primer (SEQ ID NO. 2) are represented in the sequences SEQ ID NOS. 51-52. Usually, the sequence variations tend to be introduced at the 5' end of the oligonucleotides so as not to compromise the amplification reaction. Conventionally, supplementary nucleotides can, for example, be introduced at the 5' end of the oligonucleotides.

The expression "sequence capable of selectively hybridizing" or "oligonucleotide capable of selectively hybridizing" is intended to mean, according to the invention, the sequences which hybridize with the reference sequence at a level significantly higher than the background noise. The level of the signal generated by the interaction between the sequence capable of selectively hybridizing and the reference sequences is generally ten times, preferably one hundred times stronger than that of the interaction of the other DNA sequences generating the background noise. The stringent hybridization conditions which allow selective hybridization are known to those skilled in the art. Generally, the hybridization and washing temperature is at least 5° C., for example 10° C., below the Tm of the reference sequence at a given pH and for a given ionic strength. Typically, the hybridization temperature is at least 30° C. for a polynucleotide of 15 to 50 nucleotides and at least 60° C. for a polynucleotide of more than 50 nucleotides. By way of example, the hybridization is carried out in the following buffer: 6×SSC, 50 mM Tris-HCl (pH 7.5), 1 mM EDTA, 0.02% PVP, 0.02% Ficoll, 0.02% BSA, 500 µg/ml of denatured salmon sperm DNA. The washes are, for example, carried out successively at low stringency in a 2×SSC, 0.1% SDS buffer, at medium stringency in a 0.5×SSC, 0.1% SDS buffer and at high stringency in a 0.1×SSC, 0.1% SDS buffer. The hybridization may, of course, be carried out according to other usual methods known to those skilled in the art (see, in particular, Sambrook, Fristsch and Maniatis, in their manual entitled "Molecular cloning: a laboratory manual", published by: Cold Spring Harbor Laboratory Press, Cold Spring Harbor, N.Y., 1989).

The term "stringency" is intended to mean the rigor of the operating conditions (in particular the temperature and the ionic strength) under which a molecular hybridization takes place.

The determining parameter in the specificity and the reversibility of molecular hybridization is the Tm or melting temperature. This is the temperature at which half the DNA is in single-stranded form and the other half in double-stranded form. The Tm depends on many factors, such as the length of the DNA fragment under consideration, its richness in cytosines and guanines and the salt concentration, in particular the Na ion concentration, of the reaction medium. In practice, the experimenter can create or eliminate the molecular hybridization by choosing a reaction medium temperature below, equal to or above the Tm. High stringency conditions are those for which the hybridization and washing temperature is at least 5° C., and up to at least 10° C., below the Tm of the reference sequence at a given pH and for a given ionic strength.

The term "amplification" is intended to mean any in vitro enzymatic amplification of a defined DNA sequence, in particular of the polymerase chain reaction (PCR) type.

The primers as claimed in the invention may also comprise tags which will make it possible to rapidly identify the starting sample to which each amplified sequence belongs. The term "tail" can be used in an equivalent manner, in place of the term "tag". Tags are short nucleotide sequences, generally less than ten nucleotides in length. These tags are particularly useful when it is a question of using new-generation sequencers which make it possible to sequence close to 100 000 sequences at a time. Indeed, since each tag corresponds to a starting sample to be analyzed, it is thus possible to mix several amplification products before carrying out the sequencing. This is advantageous since carrying out sequencing via a new-generation sequencer can prove to be an expensive operation. In practice, the primers as claimed in the invention may comprise an additional nucleotide fragment on the 5' side, which is specific for each sample. After amplification of several samples, mixing of the various amplification products thus obtained, and sequencing, each amplified sequence is thus easily assigned to a starting sample. The tags thus constitute a particularly advantageous tool when it is a question of high-throughput sequencing (Binladen et al., 2007).

Usually, the amplification comprises successive amplification cycles (generally from 20 to 40) which are themselves composed of three phases: after a step of denaturation (separation of the two strands of the double helix) of the DNA, the placing of the primers (specifically selected short oligonucleotide sequences) opposite the sequences complementary thereto, on the DNA strands, and the binding of said primers to these targets, constitutes the second phase of the process (hybridization). The extension phase involves an enzyme, DNA polymerase, which synthesizes, from the primers, the strand complementary to that which was used as template. Repetition of this cycle results in exponential amplification of the DNA fragment, also called amplification product or amplified DNA. According to one aspect of the invention, the hybridization is carried out at a temperature of between 45 and 65° C. In particular, the hybridization can be carried out at a temperature of between 45 and 60° C. when the primers do not comprise a tag. Alternatively, the hybridization can be carried out at a temperature of between 50 and 65° C. when the primers comprise a tag.

According to another aspect, the invention relates to a pair of oligonucleotides, according to which the first oligonucleotide selectively hybridizes to the sequence SEQ ID NO. 4 and the second nucleotide selectively hybridizes to the sequence SEQ ID NO. 5 under sufficient stringency conditions for the amplification of a variable region of the mitochondrial 12S gene of *Rana nigromaculata*, the sequence of which is represented in SEQ ID NO. 29 and which can be used as *batrachian* reference sequence.

According to another aspect, the invention relates to a pair of oligonucleotides, according to which the first oligonucleotide selectively hybridizes to the sequence SEQ ID NO. 4 and the second nucleotide selectively hybridizes to the sequence SEQ ID NO. 6 under sufficient stringency conditions for the amplification of a variable region of the mitochondrial 12S gene of *Gadus morhua*, the sequence of which is represented in SEQ ID NO. 39 and which can be used as fish reference sequence.

According to one aspect of the invention, the pair of oligonucleotides allows the amplification of a region of the mitochondrial 12S gene which comprises less than 95 nucleotides, in particular less than 90 or less than 80 nucleotides, primers not included (i.e. without counting the length of the primers). Having a universal pair of primers which allows the amplification of a short variable region is very advantageous since the use of such primers in complex or degraded substrates allows the detection and, if required, the identification of the species in such substrates.
The primers of the present invention make it possible to detect and identify more than 4012 batrachian and fish species. Tables 1 and 2 represent some of the sequences capable of being amplified with the primers of the present invention. According to one aspect of the present invention, the region amplified by polymerase chain reaction has a nucleotide sequence selected from the group consisting of any one of SEQ ID NOS. 14-48.

The present invention also relates to a mixture of primers for the amplification of a variable region of the mitochondrial 12S gene of vertebrates by polymerase chain reaction (PCR), comprising the BT_F (SEQ ID NO. 1), B_R (SEQ ID NO. 2) and T_R (SEQ ID NO. 3) amplification primers. According to one aspect of the invention, the mixture also comprises a blocking primer according to SEQ ID NO. 7. Alternatively, the invention also relates to a mixture of primers for the amplification of a variable region of the mitochondrial 12S gene of vertebrates by polymerase chain reaction (PCR), comprising the BT_F and B_R or T_R amplification primers and at least one other pair of oligonucleotides chosen from the following pairs of primers:
   amplification primers according to SEQ ID NO. 8 and SEQ ID NO. 9, optionally with a blocking primer according to SEQ ID NO. 10; and
   amplification primers according to SEQ ID NO. 11 and SEQ ID NO. 12, optionally with a blocking primer according to SEQ ID NO. 13.

Methods Using the Pair of Oligonucleotides

The present invention also relates to a method for amplifying a region of the mitochondrial 12S gene of batrachians/fish, comprising the following steps:
   a) a sample containing *batrachian*/fish DNA is provided;
   b) an amplification chain reaction is carried out using a pair of oligonucleotides as claimed in the invention.

The sample on which the amplification reaction is carried out can be collected from the environment. In this case, it may, for example, be a soil, water or feces sample. The sample may also come from industry, for example mass-produced ready meals (transformed foods) from the food industry. The sample in question may, for example, come from a product which has been frozen, lyophilized or heated. One advantage of the method as claimed in the invention using the primers described above is that the DNA contained in the sample can be in degraded form. This is mainly due to the fact that the primers have been selected such that the region amplified is short, for example less than 95 base pairs in length.

According to one aspect of the invention, the hybridization is carried out at a temperature of between 45 and 65° C. Depending on whether or not the pairs of oligonucleotides of the invention comprise a tag as is previously described, the amplification conditions, in particular the hybridization temperature, may or may not vary. In particular, the hybridization can be carried out at a temperature of between 45 and 60° C. when the primers do not comprise a tag. For example, a temperature of 51-53° C. can be used. Alternatively, the hybridization can be carried out at a temperature of between 50 and 65° C. when the primers comprise a tag. For example, a temperature of 57-58° C. can be used. Those skilled in the art know how to adapt the hybridization temperature to the primers used.

The amplification method as claimed in the invention may require a DNA extraction step before carrying out the amplification. A commercially available extraction kit is then used, for example, for this.

The present invention also provides a method for detecting a *batrachian*/fish species in a sample. This detection method as claimed in the invention comprises the following steps:
   a) a sample which may contain DNA of *batrachian*/fish species is provided;
   b) the total DNA contained in the sample is isolated;
   c) an amplification chain reaction is carried out using a pair of oligonucleotides as claimed in the invention; and
   d) the possible presence of an amplification product is detected.

The invention also relates to a method for detecting and identifying a *batrachian*/fish species in a sample, comprising the following steps:
   a) a sample which may contain DNA of *batrachian*/fish species is provided;
   b) the total DNA contained in the sample is isolated;
   c) an amplification chain reaction is carried out using a pair of oligonucleotides as claimed in the invention;
   d) the presence of an amplification product is detected; and
   e) the sequence of the amplification product is determined in order to identify the *batrachian*/fish species contained in the sample.

The step of determining the sequence corresponds to the sequencing thereof. The sequencing methods and tools are known to those skilled in the art and an example of what can be used in the present invention is given in the experimental section.

Detection Kit

The invention also relates to a kit for the detection of a *batrachian*/fish species in a sample, said kit comprising a pair of oligonucleotides as claimed in the invention.

According to one aspect of the invention, the kit also comprises a blocking primer according to SEQ ID NO. 7. It is useful to employ a blocking primer when it is a question of avoiding the amplification of a predetermined species, for example human being or cow. These primers are selected from the most variable end of the fragment amplified, and in such a way that the blocking primer overlaps with the amplification primer over at least six nucleotides, for example over eight nucleotides. Finally, it is necessary for the Tm of the blocking primer to be much higher than that of the amplification primers (at least 5° C., for example 10° C., higher).

According to yet another aspect of the invention, the kit comprises at least one other pair of oligonucleotides. This at least one other pair of oligonucleotides can then be used by way of verification of the content of the sample or by way of alternatives, for example if the pair of oligonucleotides BT_F (SEQ ID NO. 1) and B_R (SEQ ID NO. 2) or B_R (SEQ ID NO. 3) did not allow amplification.

According to yet another aspect of the invention, the kit also comprises a tag of less than ten nucleotides for the identification of the starting sample after sequencing of the PCR product.

The kit as claimed in the invention may also contain, in a nonlimiting manner, additional reagents, for example a DNA polymerase enzyme, dNTPs, Tris-HCl, KCl, MgCl$_2$ or bovine serum albumin (BSA).

Uses

The present invention also relates to the use of the variable region of the mitochondrial 12S gene of batrachians corresponding to positions 3542 to 3595 of the mitochondrial gene of *Rana nigromaculata* (NC_002805), for detecting and/or identifying *batrachian*/fish species.

The present invention also relates to the use of the variable region of the mitochondrial 12S gene of fish corresponding to positions 921 to 982 of the mitochondrial gene of *Gadus morhua* (NC_002081), for detecting and/or identifying *batrachian*/fish species.

For example, this variable region is selected from the group consisting of SEQ ID NOS. 14-48. On the basis of the sequence of the 12S gene of *Rana nigromaculata* or of *Gadus morhua* and of the positions indicated, those skilled in the art know how to identify the corresponding sequences in other *batrachian*/fish species.

Examples

Example 1: Validation of the BT_F and B_R Primers by Electronic PCR Using the ecoPCR Software (Ficetola et al. 2010)

This experiment was carried out with EMBL version 107, tolerating a maximum number of three mismatches per primer.

Results: the total number of *batrachian* sequences amplified is 5501, including 2837 unique sequences corresponding to 2106 species and 357 genera.

The length of the amplified fragment (without the primers) ranges between 16 and 71 base pairs, with an average of 50.6 base pairs.

The average number of mismatches is 0.16 for the BT_F primer, and 0.48 for the B_R primer.

Discussion: Given that the number of unique sequences is much higher than the number of species, this indicates that the resolution of this region allows, in the vast majority of cases, an identification at species level.

Example 2: Validation of the BT_F and T_R Primers by Electronic PCR Using the ecoPCR Software (Ficetola et al. 2010)

This experiment was carried out with EMBL version 107, tolerating a maximum number of three mismatches per primer.

Results: the total number of teleost sequences amplified is 2742, including 1929 unique sequences corresponding to 1906 species and 357 genera.

The length of the amplified fragment (without the primers) ranges between 48 and 91 base pairs, with an average of 63.4 base pairs.

The average number of mismatches is 0.21 for the BT_F primer, and 0.35 for the T_R primer.

Discussion: Given that the number of unique sequences is slightly higher than the number of species, this indicates that the resolution of this region allows, in the majority of cases, an identification at species level.

TABLE 1

Batrachians
Table produced using version 107 of the EMBL database

| Scientific name | Accession number | Sequence corresponding to BT_F | Sequence amplified | Sequence corresponding to B_R |
|---|---|---|---|---|
| *Allobates brunneus* | DQ502047 | ACACCGCCCGTCACCCT (SEQ ID NO. 53) | CCTCTTATACTAAAAATAGTTTT TAACCAAATTCAGCCAATCAGAA GAGGT (SEQ ID NO. 14) | GTATACTTACCATGTTACGAC TT (SEQ ID NO. 54) |
| *Alytes obstetricans* | AY364340 | ACACCGCCCGTCACCCT (SEQ ID NO. 55) | CCTCAACTAACTCAACCCCCTAA TTAAAAACTAACCAGTTAACAAG AAGAGGC (SEQ ID NO. 15) | GTATACTTACCATGTTACCAC TT (SEQ ID NO. 56) |
| *Bombina bombina* | AY458591 | ACACCGCCCGTCACCCT (SEQ ID NO. 57) | CTTCAACTAAACCAACACAATTT TTAATACACAAAATAAGTAAAAG AACACGT (SEQ ID NO. 16) | GTATACTTACCATGTTACGAC TT (SEQ ID NO. 58) |
| *Bombina variegata* | AY971143 | ACACCGCCCGTCACCCT (SEQ ID NO. 59) | CTTCAACTAGAACTGATATATTT CTAAAACATAAAACGAGTACAAG AAGAGGT SEQ ID NO. 17) | GTATACTTACCATGTTACGAC TT (SEQ ID NO. 60) |
| *Bufo bufo* | AY325988 | ACACCGCCCGTCACCCT (SEQ ID NO. 61) | CTTCAAAGCTACTAACCTAGTTT CTAACAAACTAAAGCATAACAGA AGAGGC (SEQ ID NO. 18) | GTATACTTACCATGTTACGAC TT (SEQ ID NO. 62) |
| *Bufo calamita* | EU938400 | ACACCGCCCGTCACCCT (SEQ ID NO. 63) | CTTCAAGGCACTGACATAGTTTT TAACTAACTTAAGCAAAACGAAA GAGGC (SEQ ID NO. 19) | GTATACTTACCATGTTACGAC TT (SEQ ID NO. 64) |

TABLE 1-continued

Batrachians
Table produced using version 107 of the EMBL database

| Scientific name | Accession number | Sequence corresponding to BT_F | Sequence amplified | Sequence corresponding to B_R |
|---|---|---|---|---|
| Bufo viridis | AY680267 | ACACCGCCCGTCACCCT (SEQ ID NO. 65) | CTTCAAAGCATAAACAAAGTTTT TAACAAGTTTGAGCATAACAGAA GAGGC (SEQ ID NO. 20) | GTATACTTACCATGTTACGAC TT (SEQ ID NO. 66) |
| Dendrobates auratus | AY326030 | ACACCGCCCGTCACCCT (SEQ ID NO. 67) | CCTCAACGCTATTTTAAAGTTTC TTACACATTTTAGCTGCATAGAA GAGGC (SEQ ID NO. 21) | GTATACTTACCATGTTACGAC TT (SEQ ID NO. 68) |
| Dendrobates tinctorius | DQ502248 | ACACCGCCCGTCACCCT (SEQ ID NO. 69) | CCTCAACGCTACTTTAAAGTTTC TCACATACCTTACCTACATAGAA GAGGC (SEQ ID NO. 22) | GTACACTTACCATGTTACGAC TT (SEQ ID NO. 70) |
| Discoglossus pictus | AY364342 | ACACCGCCCGTCACCCT (SEQ ID NO. 71) | CTTCAACCCGCCGTATTCAAGTA TTTAAATAATTTTGGCAAAAAAG AAGAGGC (SEQ ID NO. 23) | GTATACTTACCATGTTACGAC TT (SEQ ID NO. 72) |
| Hyla arborea | AYE43681 | ACACCGCCCGTCACCCT (SEQ ID NO. 73) | CTTCAAAGCCCCGTATTAGTAAT TAACTTAACTTAGCAAATCAGAA GAGGC (SEQ ID NO. 24) | GTACGCTTACCATGTTACGAC TT (SEQ ID NO. 74) |
| Hyla meridionalis | AYE19370 | ACACCGCCCGTCACCCT (SEQ ID NO. 75) | CTTCAAAGCCTAAACATCAGTAA TTAACTCAAACTAGCACACCAGA AGAGGC (SEQ ID NO. 25) | GTACGCTTACCATGTTACGAC TT (SEQ ID NO. 76) |
| Plethodon cinerues | AY728232 | ACACCGCCCGTCACCCT (SEQ ID NO. 77) | CATCAAATATATTACTTTAGAAG ACGA (SEQ ID NO. 26) | GTAGGCTTACCATGTTACGAC TT (SEQ ID NO. 78) |
| Pleurodeles poireti | EU880329 | ACACCGCCCGTCACCCT (SEQ ID NO. 79) | CTTCAAACAATATAAAAACCCTA TATAAACAGAAATAAAAGAAAGA AGAGGC (SEQ ID NO. 27) | GTAGACTTACCATGTTACGAC TT (SEQ ID NO. 80) |
| Rana catesbeiana | AY779206 | ACACCGCCCGTCACCCT (SEQ ID NO. 81) | CTTCGATAGTATCTCACCCCGTT CCTAACCCACTATTACATTTTAG AAGAGGC (SEQ ID NO. 28) | GTACACTTACCATGTTACGAC TT (SEQ ID NO. 82) |
| Rana nigromaculata | NC_002805 | | CTTCGATAGCACTTCACCCAGGT ATTTAACCCAATACCGCATCTTA GAAGAGGC (SEQ ID NO. 29) | |
| Rana pipiens | AY779221 | ACACCGCCCGTCACCCT (SEQ ID NO. 83) | CTTCGATAGTAAATAATATTGTC CCTAACCCATTATCACGTTTTAG AAGAAGC (SEQ ID NO. 30) | GTACACTTACCATGTTTCGAC TT (SEQ ID NO. 84) |
| Rana temporaria | AF249023 | ACACCGCCCGTCACCCT (SEQ ID NO. 85) | CTTCAATAGTACCCCGTATGTTC CTAACCCAACACCACGTTTTAGA AGAGGC (SEQ ID NO. 31) | GTACACTTACCATGTTACGAC TT (SEQ ID NO. 86) |
| Salamandra salamandra | DQ283440 | ACACCGCCCGTCACCCT (SEQ ID NO. 87) | CTTCAAATAATTTAAAAAAATCT TAAATAAATAAAGTCAGTAAGTA AGAAGAGGC (SEQ ID NO. 32) | GTAGACTTACCATGTTACGAC TT (SEQ ID NO. 88) |
| Triturus cristatus | DQ283441 | ACACCGCCCGTCACCCT (SEQ ID NO. 89) | CTTCAAGAACTATTAGATATTAA ATAAACAAAGAAGAAAAAAGAAG AAGAGGC (SEQ ID NO. 33) | GTAAACTTACCATGTTACGAC TT (SEQ ID NO. 90) |

TABLE 1-continued

Batrachians
Table produced using version 107 of the EMBL database

| Scientific name | Accession number | Sequence corresponding to BT_F | Sequence amplified | Sequence corresponding to B_R |
|---|---|---|---|---|
| Triturus marmoratus | EU880337 | ACACCGCCCGTCACCCT (SEQ ID NO. 91) | CTTCAAGCACTATTTTATATTAA ATAAACAAAAGAAAAAAGAAGA AGAGGC (SEQ ID NO. 34) | GTAAACTTACCATGTTACGAC TT (SEQ ID NO. 92) |

TABLE 2

Teleost fish
Table produced using version 107 of the EMBL database

| Scientific name | Accession number | Sequence corresponding to BT_F | Sequence amplified | Sequence corresponding to T_R |
|---|---|---|---|---|
| Anguilla anguilla | AB021887 | ACACCGCCCGTCACTCT (SEQ ID NO. 93) | CCTCGAATAACAATAAAGACAAT TCATAAAACAATAAGAACAAAAA GAGGAGGCAAGTCGTAA (SEQ ID NO. 35) | CTTCCGGTACACTTACCGTG (SEQ ID NO. 94) |
| Barbus barbus | AB238965 | ACACCGCCCGTCACTCT (SEQ ID NO. 95) | CCCCGTCAAAATGCACCAAAATA CCTAATGCAACAGCACTGACAAG GGGGAGGCAAGTCGTAA (SEQ ID NO. 36) | CTTCCGGTACACTTACCATG (SEQ ID NO. 96) |
| Clupea harengus | AP009133 | ATACCGCCCGTCACTCT (SEQ ID NO. 97) | CCCCAGCGACCACCCAAAAAAGG TAAATAACGCAATAATAACAGCA AGGGGAGGCAAGTCGTAA (SEQ ID NO. 37) | CTTCCGGTATACTTACCATG (SEQ ID NO. 98) |
| Exocoetus volitans | AP002933 | ACACCGCCCGTCACCCT (SEQ ID NO. 99) | CCCCAAAACCCTAAAAAGATTA AGTAAAACCATAGATCCAATAAA GGGGAGGCAAGTCGTAA (SEQ ID NO. 38) | CTTCCGGTACACTTACCATG (SEQ ID NO. 100) |
| Gadus morhua | AM489716 | ACACCGCCCGTCACTCT (SEQ ID NO. 101) | CTCCAAATAAACCCTAGATATTA CCTAAAATGCTTTTTATAATAAG GGGAGGCAAGTCGTAA (SEQ ID NO. 39) | CTTCCGGTACGCTTACCATG (SEQ ID NO. 102) |
| Hippocampus coronatus | AB032030 | ACACCGCCCGTCACTCT (SEQ ID NO. 103) | CCCTAAAACACACTTAAAACTAA TTAAAACAAAATATTAAACAAGG GGAGGCAAGTCGTAA (SEQ ID NO. 40) | CTTCCGGTACGCTTACCATG (SEQ ID NO. 104) |
| Labrus merula | AJ810141 | ACACCGCCCGTCACTCT (SEQ ID NO. 105) | CCCCGAGCTTACGTATCTTAATA CTTAATCCCTTATAATTGCAAAG GGGAGGCAAGTCGTAA (SEQ ID NO. 41) | CTTCCGGTACACTTACCAGT (SEQ ID NO. 106) |
| Lota lota | AP004412 | ACACCGCCCGTCACTCT (SEQ ID NO. 107) | CTCCAAATAGACCCTAAATATTA CCTAAAATGTTTTATATAATAAC GGGAGGCAAGTCGTAA (SEQ ID NO. 42) | CTTCCGGTACGCTTACCATG (SEQ ID NO. 108) |
| Oncorhynchus mykiss | AF113120 | ACACCGCCCGTCACTCT (SEQ ID NO. 109) | CCCCAAGTTCAACCTGTCCTTCT AACTAAGAAGTTAACCGAACAAA GGGGAGGCAAGTCGTAA (SEQ ID NO. 43) | CTTCCGGTACACTTACCATG (SEQ ID NO. 110) |
| Salmo trutta | AM910449 | ACACCGCCCGTCACTCT (SEQ ID NO. 111) | CCCCGAGTTCAATTAATCCTTCT AACTAAGAAGTTAACCGAACAAA GGGGAGGCAAGTCGTAA (SEQ ID NO. 44) | CTTCCGGTACACTTACCATG (SEQ ID NO. 112) |
| Salvelinus alpinus | AF154851 | ACACCGCCCGTCACTCT (SEQ ID NO. 113) | CCCCAAGTTTAATTTATCCTTCT AACTAAGAAGTTAACCAAACAAA GGGGAGGCAAGTCGTAA (SEQ ID NO. 45) | CTTCCGGTACACTTACCATG (SEQ ID NO. 114) |

TABLE 2-continued

Teleost fish
Table produced using version 107 of the EMBL database

| Scientific name | Accession number | Sequence corresponding to BT_F | Sequence amplified | Sequence corresponding to T_R |
|---|---|---|---|---|
| *Salvelinus fontinalis* | AF154850 | ACACCGCCCGTCACTCT (SEQ ID NO. 115) | CCCCAAGTTTAATTTATCCTTCT AACTAAGAAGTTAACCAAACAAA GGGGAGCCAAGTCGTAA (SEQ ID NO. 46) | CTTCCGGTACACTTACCATG (SEQ ID NO. 116) |
| *Sardina pilchardus* | AP009233 | ACACCGCCCGTCACTCT (SEQ ID NO. 117) | CCCCAACAACTACCTATAAAAAT GTAACTAACACAATATTCGCCCC AAGGGGAGGCAAGTCGTAA (SEQ ID NO. 47) | CTTCCGGTACACTTACCATG (SEQ ID NO. 118) |
| *Zeus faber* | AP002941 | ACACCGCCCGTCACTCT (SEQ ID NO. 119) | CCCCTGTTGGCCCCCAACCTTTC ATAAAACCTTTATTAAACAAAGG GGAGGCAAGTCGTAA (SEQ ID NO. 48) | CTTCCGGTACGGTTACCATG (SEQ ID NO. 120) |

---

The invention claimed is:

1. A method for amplifying a region of the mitochondrial 12S gene of *batrachian* and fish species, comprising the following steps:
   a) a sample suspected of containing DNA from a *batrachian* and/or fish species is provided, the *batrachian* species is a part of the *batrachian* kingdom of amphibia;
   b) an amplification chain reaction is carried out using a pair of oligonucleotides, according to which the first oligonucleotide selectively hybridizes to the sequence SEQ NO. 4 and the second oligonucleotide selectively hybridizes to the sequence SEQ ID NO. 5 or to the sequence SEQ ID NO. 6.

2. A method for detecting a *batrachian* and/or fish species in a sample, comprising the following steps:
   a) a sample suspected of containing DNA from a *batrachian* and/or fish species is provided, the *batrachian* species is a part of the *batrachian* kingdom of amphibia;
   b) the total DNA contained in the sample is isolated;

c) an amplification chain reaction is carried out using a pair of oligonucleotides, according to which the first oligonucleotide selectively hybridizes to the sequence SEQ NO. 4 and the second oligonucleotide selectively hybridizes to the sequence SEQ ID NO. 5 or to the sequence SEQ ID NO. 6; and d) the possible presence of an amplification product is detected.

3. A process for detecting and identifying a *batrachian* and/or fish species in a sample, comprising the following steps:

a) a sample suspected of containing DNA from a *batrachian* and/or fish species is provided, the *batrachian* species is a part of the *batrachian* kingdom of *amphibia;* b) the total DNA contained in the sample is isolated;

c) an amplification chain reaction is carried out using a pair of oligonucleotides, according to which the first oligonucleotide selectively hybridizes to the sequence SEQ NO. 4 and the second oligonucleotide selectively hybridizes to the sequence SEQ ID NO. 5 or to the sequence SEQ ID NO. 6;

d) the presence of an amplification product is detected; and e) the sequence of the amplification product is determined in order to identify the *batrachian* and/or fish species contained in the sample.

4. The method of claim 1, according to which the first oligonucleotide has a nucleotide sequence SEQ ID NO. 1 and the second oligonucleotide has a nucleotide sequence SEQ ID NO. 2 or SEQ ID NO. 3.

5. The method of claim 1, further comprising the amplification chain reaction carried out with a blocking primer according to SEQ ID NO. 7.

6. The method of claim 2, according to which the first oligonucleotide has a nucleotide sequence SEQ ID NO. 1 and the second oligonucleotide has a nucleotide sequence SEQ ID NO. 2 or SEQ ID NO. 3.

7. The method of claim 2, further comprising the amplification chain reaction carried out with a blocking primer according to SEQ ID NO. 7.

8. The method of claim 3, according to which the first oligonucleotide has a nucleotide sequence SEQ ID NO. 1 and the second oligonucleotide has a nucleotide sequence SEQ ID NO. 2 or SEQ ID NO. 3.

9. The method of claim 3, further comprising the amplification chain reaction carried out with a blocking primer according to SEQ ID NO. 7.

* * * * *

SEQUENCE LISTING

<160> NUMBER OF SEQ ID NOS: 52

<210> SEQ ID NO 1
<211> LENGTH: 17
<212> TYPE: DNA
<213> ORGANISM: Artificial Sequence
<220> FEATURE:
<223> OTHER INFORMATION: primer

<400> SEQUENCE: 1
acaccgcccg tcacyct                              17

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
gtayacttac catgttacga ctt                       23

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cttccggtac acttaccatg                           20

<210> SEQ ID NO 4
<211> LENGTH: 17
<212> TYPE: DNA
<213> ORGANISM: Artificial Sequence
<220> FEATURE:
<223> OTHER INFORMATION: sequence complementary to a primer

<400> SEQUENCE: 4
agrgtgacgg gcggtgt                              17

```
<210> SEQ ID NO 5
<211> LENGTH: 23
<212> TYPE: DNA
<213> ORGANISM: Artificial Sequence
<220> FEATURE:
<223> OTHER INFORMATION: sequence complementary to a primer

<400> SEQUENCE: 5
aagtcgtaac atggtaagtr tac                                              23

<210> SEQ ID NO 6
<211> LENGTH: 20
<212> TYPE: DNA
<213> ORGANISM: Artificial Sequence
<220> FEATURE:
<223> OTHER INFORMATION: sequence complementary to a primer

<400> SEQUENCE: 6
catggtaagt gtaccggaag                                                  20

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
tcaccctcct caagtatact tcaaaggaca                                       30

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gggattagat accccactat                                                  20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
tcaagtcctt tgggttttaa g                                                21

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
ccactatgct tagccctaaa cctcaacag                                        29

<210> SEQ ID NO 11
<211> LENGTH: 21
<212> TYPE: DNA
<213> ORGANISM: Artificial Sequence
<220> FEATURE:
<223> OTHER INFORMATION: primer
```

<400> SEQUENCE: 11
cgagaagacc ctatggagct t                                           21

<210> SEQ ID NO 12
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t

<400> SEQUENCE: 12
cryggtcgcc ccaaccnaaa                                             20

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
tggagcttta atttattaat gcaaacagta cctaacaaa                        39

<210> SEQ ID NO 14
<211> LENGTH: 51
<212> TYPE: DNA
<213> ORGANISM: Allobates brunneus

<400> SEQUENCE: 14
cctcttatac taaaaatagt ttttaaccaa attcagccaa tcagaagagg t           51

<210> SEQ ID NO 15
<211> LENGTH: 53
<212> TYPE: DNA
<213> ORGANISM: Alytes obstetricans

<400> SEQUENCE: 15
cctcaactaa ctcaaccccc taattaaaaa ctaaccagtt aacaagaaga ggc         53

<210> SEQ ID NO 16
<211> LENGTH: 53
<212> TYPE: DNA
<213> ORGANISM: Bombina bombina

<400> SEQUENCE: 16
cttcaactaa accaacacaa tttttaatac acaaaataag taaagaaga ggt          53

<210> SEQ ID NO 17
<211> LENGTH: 53
<212> TYPE: DNA
<213> ORGANISM: Bombina variegata

<400> SEQUENCE: 17
cttcaactag aactgatata tttctaaaac ataaaacgag tacaagaaga ggt         53

<210> SEQ ID NO 18
<211> LENGTH: 52
<212> TYPE: DNA
<213> ORGANISM: Bufo bufo

-continued

```
<400> SEQUENCE: 18
cttcaaagct actaacctag tttctaacaa actaaagcat aacagaagag gc        52

<210> SEQ ID NO 19
<211> LENGTH: 51
<212> TYPE: DNA
<213> ORGANISM: Bufo calamita

<400> SEQUENCE: 19
cttcaaggca ctgacatagt ttttaactaa cttaagcaaa acagaagagg c         51

<210> SEQ ID NO 20
<211> LENGTH: 51
<212> TYPE: DNA
<213> ORGANISM: Bufo viridis

<400> SEQUENCE: 20
cttcaaagca taaacaaagt ttttaacaag tttgagcata acagaagagg c         51

<210> SEQ ID NO 21
<211> LENGTH: 51
<212> TYPE: DNA
<213> ORGANISM: Dendrobates auratus

<400> SEQUENCE: 21
cctcaacgct attttaaagt ttcttacaca ttttagctgc atagaagagg c         51

<210> SEQ ID NO 22
<211> LENGTH: 51
<212> TYPE: DNA
<213> ORGANISM: Dendrobates tinctorius

<400> SEQUENCE: 22
cctcaacgct actttaaagt ttctcacata ccttagctac atagaagagg c         51

<210> SEQ ID NO 23
<211> LENGTH: 53
<212> TYPE: DNA
<213> ORGANISM: Discoglossus pictus

<400> SEQUENCE: 23
cttcaacccg ccgtattcaa gtatttaaat aattttggca aaaagaaga ggc        53

<210> SEQ ID NO 24
<211> LENGTH: 51
<212> TYPE: DNA
<213> ORGANISM: Hyla arborea

<400> SEQUENCE: 24
cttcaaagcc cggtattagt aattaactta acttagcaaa tcagaagagg c         51

<210> SEQ ID NO 25
<211> LENGTH: 52
<212> TYPE: DNA
<213> ORGANISM: Hyla meridionalis

<400> SEQUENCE: 25
cttcaaagcc taaacatcag taattaactc aaactagcac accagaagag gc        52

<210> SEQ ID NO 26
<211> LENGTH: 27
<212> TYPE: DNA
<213> ORGANISM: Plethodon cinereus
```

```
<400> SEQUENCE: 26
catcaaatat attactttag aagagga                                        27

<210> SEQ ID NO 27
<211> LENGTH: 52
<212> TYPE: DNA
<213> ORGANISM: Pleurodeles poireti

<400> SEQUENCE: 27
cttcaaacaa tataaaaacc ctatataaac agaaataaaa gaaagaagag gc            52

<210> SEQ ID NO 28
<211> LENGTH: 53
<212> TYPE: DNA
<213> ORGANISM: Rana catesbeiana

<400> SEQUENCE: 28
cttcgatagt atctcaccccc gttcctaacc cactattaca ttttagaaga ggc          53

<210> SEQ ID NO 29
<211> LENGTH: 54
<212> TYPE: DNA
<213> ORGANISM: Rana nigromaculata

<400> SEQUENCE: 29
cttcgatagc acttcaccca ggtatttaac ccaataccgc atcttagaag aggc          54

<210> SEQ ID NO 30
<211> LENGTH: 53
<212> TYPE: DNA
<213> ORGANISM: Rana pipiens

<400> SEQUENCE: 30
cttcgatagt aaataatatt gtccctaacc cattatcacg ttttagaaga agc           53

<210> SEQ ID NO 31
<211> LENGTH: 52
<212> TYPE: DNA
<213> ORGANISM: Rana temporaria

<400> SEQUENCE: 31
cttcaatagt accccgtatg ttcctaaccc aacaccacgt tttagaagag gc            52

<210> SEQ ID NO 32
<211> LENGTH: 55
<212> TYPE: DNA
<213> ORGANISM: Salamandra salamandra

<400> SEQUENCE: 32
cttcaaataa tttaaaaaaa tcttaaataa ataaagtcag taagtaagaa gaggc         55

<210> SEQ ID NO 33
<211> LENGTH: 53
<212> TYPE: DNA
<213> ORGANISM: Triturus cristatus

<400> SEQUENCE: 33
cttcaagaac tattagatat taaataaaca aagaagaaaa aagaagaaga ggc           53

<210> SEQ ID NO 34
<211> LENGTH: 52
<212> TYPE: DNA
<213> ORGANISM: Triturus marmoratus
```

```
<400> SEQUENCE: 34
cttcaagcac tattttatat taaataaaca aaagaaaaa agaagaagag gc            52

<210> SEQ ID NO 35
<211> LENGTH: 63
<212> TYPE: DNA
<213> ORGANISM: Anguilla anguilla

<400> SEQUENCE: 35
cctcgaataa caataaagac aattcataaa acaataagaa caaaaagagg aggcaagtcg   60
taa                                                                63

<210> SEQ ID NO 36
<211> LENGTH: 62
<212> TYPE: DNA
<213> ORGANISM: Barbus barbus

<400> SEQUENCE: 36
ccccgtcaaa atgcaccaaa atacctaatg caacagcact gacaagggga ggcaagtcgt   60
aa                                                                 62

<210> SEQ ID NO 37
<211> LENGTH: 64
<212> TYPE: DNA
<213> ORGANISM: Clupea harengus

<400> SEQUENCE: 37
ccccagcgac cacccaaaaa aggtaaataa cgcaataata acagcaaggg gaggcaagtc   60
gtaa                                                               64

<210> SEQ ID NO 38
<211> LENGTH: 63
<212> TYPE: DNA
<213> ORGANISM: Exocoetus volitans

<400> SEQUENCE: 38
ccccaaaacc cctaaaaaga ttaagtaaaa ccatagatcc aataaagggg aggcaagtcg   60
taa                                                                63

<210> SEQ ID NO 39
<211> LENGTH: 62
<212> TYPE: DNA
<213> ORGANISM: Gadus morhua

<400> SEQUENCE: 39
ctccaaataa accctagata ttacctaaaa tgctttttat aataagggga ggcaagtcgt   60
aa                                                                 62

<210> SEQ ID NO 40
<211> LENGTH: 61
<212> TYPE: DNA
<213> ORGANISM: Hippocampus coronatus

<400> SEQUENCE: 40
ccctaaaaca cacttaaaac taattaaaac aaaatattaa acaaggggag gcaagtcgta   60
a                                                                  61
```

-continued

```
<210> SEQ ID NO 41
<211> LENGTH: 62
<212> TYPE: DNA
<213> ORGANISM: Labrus merula

<400> SEQUENCE: 41
ccccgagctt acgtatctta atacttaatg ccttataatt gcaaagggga ggcaagtcgt      60
aa                                                                    62

<210> SEQ ID NO 42
<211> LENGTH: 62
<212> TYPE: DNA
<213> ORGANISM: Lota lota

<400> SEQUENCE: 42
ctccaaatag accctaaata ttacctaaaa tgttttatat aataagggga ggcaagtcgt      60
aa                                                                    62

<210> SEQ ID NO 43
<211> LENGTH: 63
<212> TYPE: DNA
<213> ORGANISM: Oncorhynchus mykiss

<400> SEQUENCE: 43
ccccaagttc aacctgtcct tctaactaag aagttaaccg aacaaagggg aggcaagtcg      60
taa                                                                   63

<210> SEQ ID NO 44
<211> LENGTH: 63
<212> TYPE: DNA
<213> ORGANISM: Salmo trutta

<400> SEQUENCE: 44
ccccgagttc aattaatcct tctaactaag aagttaaccg aacaaagggg aggcaagtcg      60
taa                                                                   63

<210> SEQ ID NO 45
<211> LENGTH: 63
<212> TYPE: DNA
<213> ORGANISM: Salvelinus alpinus

<400> SEQUENCE: 45
ccccaagttt aatttatcct tctaactaag aagttaacca aacaaagggg aggcaagtcg      60
taa                                                                   63

<210> SEQ ID NO 46
<211> LENGTH: 63
<212> TYPE: DNA
<213> ORGANISM: Salvelinus fontinalis

<400> SEQUENCE: 46
ccccaagttt aatttatcct tctaactaag aagttaacca aacaaagggg aggcaagtcg      60
taa                                                                   63

<210> SEQ ID NO 47
<211> LENGTH: 65
<212> TYPE: DNA
<213> ORGANISM: Sardina pilchardus
```

```
<400> SEQUENCE: 47
ccccaacaac tacctataaa aatgtaacta acacaatatt cgccgcaagg ggaggcaagt    60
cgtaa                                                                65

<210> SEQ ID NO 48
<211> LENGTH: 61
<212> TYPE: DNA
<213> ORGANISM: Zeus faber

<400> SEQUENCE: 48
cccctgttgg cccccaacct ttcataaaac ctttattaaa caaaggggag gcaagtcgta    60
a                                                                    61

<210> SEQ ID NO 49
<211> LENGTH: 17
<212> TYPE: DNA
<213> ORGANISM: Artificial Sequence
<220> FEATURE:
<223> OTHER INFORMATION: primer

<400> SEQUENCE: 49
acaccgcccg tcaccct                                                   17

<210> SEQ ID NO 50
<211> LENGTH: 17
<212> TYPE: DNA
<213> ORGANISM: Artificial Sequence
<220> FEATURE:
<223> OTHER INFORMATION: primer

<400> SEQUENCE: 50
acaccgcccg tcactct                                                   17

<210> SEQ ID NO 51
<211> LENGTH: 23
<212> TYPE: DNA
<213> ORGANISM: Artificial Sequence
<220> FEATURE:
<223> OTHER INFORMATION: primer

<400> SEQUENCE: 51
gtacacttac catgttacga ctt                                            23

<210> SEQ ID NO 52
<211> LENGTH: 23
<212> TYPE: DNA
<213> ORGANISM: Artificial Sequence
<220> FEATURE:
<223> OTHER INFORMATION: primer

<400> SEQUENCE: 52
gtatacttac catgttacga ctt                                            23
```